US012678267B1

(12) United States Patent
Johnson

(10) Patent No.: US 12,678,267 B1
(45) Date of Patent: Jul. 14, 2026

(54) SYSTEM AND METHOD FOR PROVIDING DENTAL SERVICES TO A PATIENT

(71) Applicant: Andrew C. Johnson, Fayetteville, AR (US)

(72) Inventor: Andrew C. Johnson, Fayetteville, AR (US)

( * ) Notice: Subject to any disclaimer, the term of this patent is extended or adjusted under 35 U.S.C. 154(b) by 301 days.

(21) Appl. No.: 18/597,125

(22) Filed: Mar. 6, 2024

Related U.S. Application Data

(63) Continuation-in-part of application No. 16/575,211, filed on Sep. 18, 2019, now abandoned.

(60) Provisional application No. 62/839,331, filed on Apr. 26, 2019.

(51) Int. Cl.
| | |
|---|---|
| *A61C 13/01* | (2006.01) |
| *A61C 9/00* | (2006.01) |
| *A61C 13/08* | (2006.01) |
| *A61C 13/10* | (2006.01) |
| *A61C 13/107* | (2006.01) |
| *A61C 13/34* | (2006.01) |
| *G16H 10/60* | (2018.01) |
| *G16H 30/20* | (2018.01) |
| *G16H 80/00* | (2018.01) |

(52) U.S. Cl.
CPC ........ *A61C 13/0001* (2013.01); *A61C 9/0053* (2013.01); *A61C 13/01* (2013.01); *A61C 13/08* (2013.01); *A61C 13/1003* (2013.01); *A61C*
*13/34* (2013.01); *G16H 10/60* (2018.01); *G16H 30/20* (2018.01); *G16H 80/00* (2018.01)

(58) Field of Classification Search
CPC ..... A61C 13/0001; A61C 13/01; A61C 13/08; A61C 13/1003; A61C 13/34; G16H 10/60; G16H 30/20; G16H 80/00
See application file for complete search history.

(56) References Cited

U.S. PATENT DOCUMENTS

| | | | |
|---|---|---|---|
| 5,427,906 A | * | 6/1995 | Hansen ................ A61C 8/0048 433/173 |
| 5,885,077 A | * | 3/1999 | Jeffer ........................ A61C 8/00 433/168.1 |
| 6,398,548 B1 | | 6/2002 | Muhammad et al. |
| 7,077,646 B2 | | 7/2006 | Hilliard |
| 7,523,044 B2 | | 4/2009 | Rosenblood |
| 10,179,035 B2 | | 1/2019 | Shivapuja et al. |
| 2008/0001572 A9 | | 1/2008 | Dunne et al. |
| 2008/0015727 A1 | * | 1/2008 | Dunne ................... B33Y 30/00 700/118 |
| 2015/0156208 A1 | | 6/2015 | Kirkham et al. |
| 2017/0281313 A1 | | 10/2017 | Kim et al. |
| 2023/0069231 A1 | * | 3/2023 | Gerth ..................... A61C 13/10 |

* cited by examiner

*Primary Examiner* — Yogesh P Patel

(74) *Attorney, Agent, or Firm* — Wright Lindsey Jennings, LLP; Meredith Lowry

(57) ABSTRACT

A system and method providing a dental patient and dental provider with a selection portal for services to allow a patient to find a provider and a provider to assess the needs and interests of the patient prior to a visit, and to provide treatment facilitating/smile preview devices for use at the initial visit.

3 Claims, 4 Drawing Sheets

SYSTEM AND METHOD FOR PROVIDING DENTAL SERVICES TO A PATIENT

CROSS-REFERENCE TO RELATED APPLICATIONS

This application claims priority to and is a continuation-in-part of U.S. application Ser. No. U.S. application Ser. No. 16/575,211, filed Sep. 18, 2019, which claims priority to and is a continuation-in-part of U.S. application Ser. No. U.S. application 62/839,331, filed Apr. 26, 2019, the entireties of which are hereby incorporated by reference.

FEDERALLY SPONSORED RESEARCH AND DEVELOPMENT

Not applicable.

BACKGROUND OF THE INVENTION

The invention is related generally to the field of prosthodontics, but allows similar applications in cosmetic dentistry, orthodontics, maxillofacial and peridontonal surgery as well. More particularly, the present invention is related to a method and system for providing and facilitating access to a digital prosthetic smile design through use of a digital platform that defines patient expectations, establishes provider patient-provider relationships, conveys initial information and produces physical devices for the efficient completion of the dental procedures which achieves those pre-designed treatment goals.

SUMMARY OF THE INVENTION

The process for obtaining dental treatment, namely prosthodontic and surgical services like dentures and/or dental implants can be a daunting process for patients and providers. For patients, the selection of a qualified provider can be confusing, and the effort and expense of the consultative/diagnostic process can be discouraging especially when the professional opinions acquired do not align with initial patient expectations. For a provider, the process of scheduling, meeting, assessing, and reviewing the needs of a prospective new patient in order to propose treatment and discuss the procedural steps can be an expense of time that the provider is unsure will pay off. Furthermore, when a patient and a provider do align on a treatment goal and the associated procedural plan, there are several preliminary steps (notably the primary dental molds and initial smile design process) that then must occur. While these steps allow for visualization and accuracy in developing and delivering expected results, they add significant time and expense to the overall treatment process. There is a need, therefore, to streamline the process while additionally providing informational and educational benefits to patients and providers respectively.

Currently, when a patient, Patient A, needs dentures, Patient A must either be referred to a dental provider or find one through directories. Patient A must then schedule and attend an initial consult and/or examination. Anyone who has sought a new doctor or dentist knows that initial consults are fraught with idle chitchat, leading to lost time by both the patient and the provider. However, the initial consult is important because Patient A must at least receive a cursory, visual assessment and have a discussion about general problems and tentative treatment options. Patient A, if she is satisfied with the provider and the treatment proposed, will then return to the dental clinic for a series of separate appointments required to accomplish all the procedural steps in creating a denture, traditionally beginning with preliminary molds of her mouth. The additional steps in the traditional denture workflow along with the usual gap between initial consult and molds can contribute to more lost time and even an opt-out or loss of customer by the provider. Only towards the end of the usual four to seven appointment process is a try-in model of the final denture available for fitting and viewing. Patient A and the doctor must review and approve the try-in to make sure Patient A and the doctor are satisfied with the appearance and the function of the dentures. If adjustments have to be made, Patient A may require another visit for a later review of the corrected try-in. Once the doctor and Patient A are satisfied, then the dentures can be completed.

In contrast, the proposed invention is a platform accessible through a computing device by a patient that provides a directory of approved dental providers. Patient B, upon accessing the portal, can upload photographs of her mouth for review by both a dental laboratory and selected providers in her preferred area of service. Involvement by the dental laboratory at this stage is atypical, but important to provide the initial dental assets for the first appointment with the patient. Initially the dental laboratory service provides the digital smile design preview in terms of modified versions of the submitted patient images. If the patient is interested in identifying and pursuing the actual dental treatment necessary to achieve that previewed smile in reality, they are then asked to prioritize their most desired dental provider attributes and rank their preferred provider selections from the list in the platform database. The providers, once presented with the images, patient information as well as the smile design preview can opt to provide service or decline service to the patient. Patient B can then agree to schedule an initial appointment with the accepting provider. Since the provider has seen Patient B's images and associated case information prior to the initial meeting, the initial appointment can more directly and visually address the patients desires rather than awkward chitchat followed by generalized and potentially discouraging professional opinions in terms of appropriate procedures, cost, timelines, etc.. With the digital images already available, the provider can then have a digital image of the prospective change to Patient B's smile for presentation to Patient B in the first meeting as well as a preemptive opportunity to offer rough cost estimates, procedural complexity and treatment timelines. With the digital images provided to the dental laboratory ahead of the clinical diagnostic appointment, the dental laboratory can prepare initial dental assets for review by the provider and ship these assets to the provider for use at the initial meeting. This upfront information supplemented with a potential treatment result visualization, will give Patient B more ability to decide if the selected provider is best suited to accomplish her treatment goals, and Patient B is more likely to present for the initial visit prepared to move forward with the treatment, thus reducing the risk of the provider losing time. In this manner, the proposed invention reduces lost time for both the patient and the provider.

In addition to the digital smile preview and preemptive two-party case approval and treatment information provided, for applicable treatment categories (like dentures, orthodontics, implants, esthetics, etc.), the approved digital smile design preview can be produced as physical objects via prototyping technologies like three-dimensional printing and utilized in the course of actual in-person diagnostics and treatment procedures. Physical recording devices and/or smile try-ins can be produced ahead of the initial appointment and made available to the patient and/or the selected provider for direct use/visualization in the first appointment. By incorporating three-dimensional scan data acquired at a participating scanning/diagnostic center with the patient photographs, a three-dimensional digital smile design can be completed and converted to physical media for use in the actual course of diagnostics and treatment. The early generation and implementation of such physical treatment renderings (smile try-ins) and recording devices (impression trays, bite registrations, etc.) so to allow for direct viewing at the front end of the patient-provider interaction can lead to more motivated patients as well as more a predictable and efficient treatment process.

These and other objects, features, and advantages of the present invention will become better understood from a consideration of the following detailed description of the preferred embodiments and appended claims in conjunction with the drawings.

DETAILED DESCRIPTION OF THE INVENTION

Figure 1:
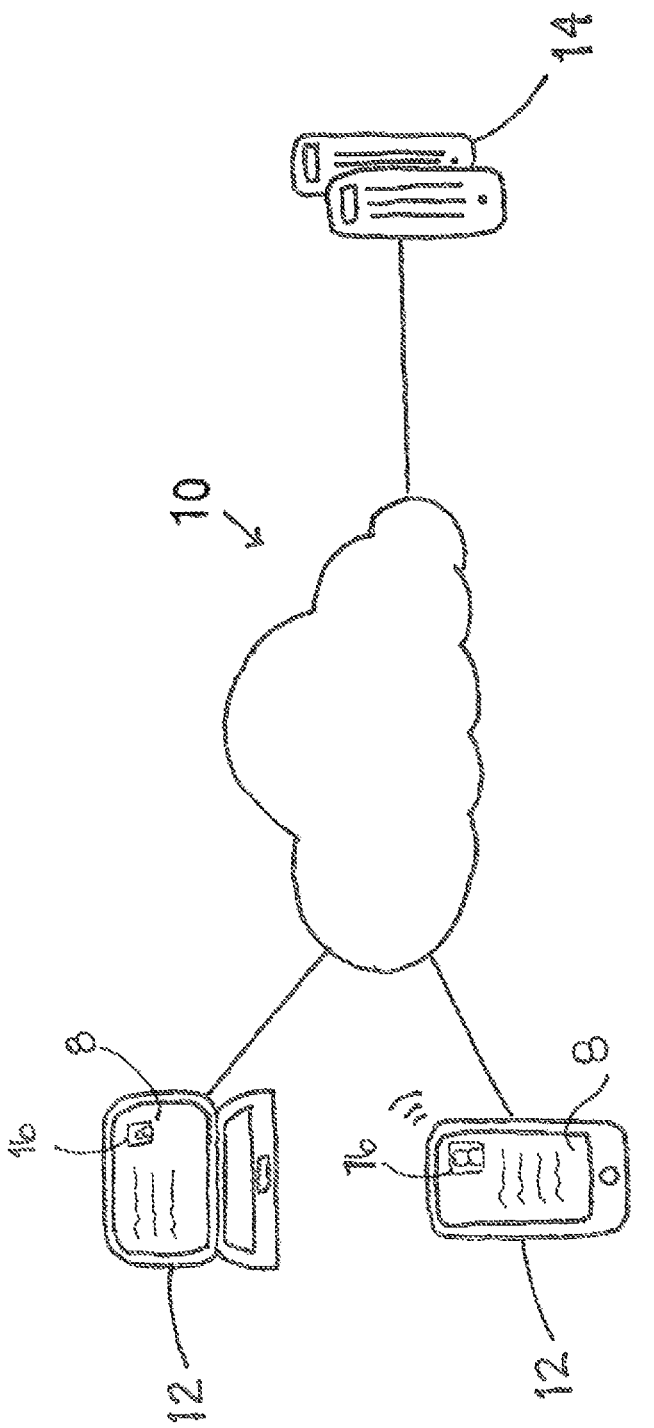
FIG. 1 is a schematic of the method of the present invention.

Generally speaking, the present invention is directed to a system and method for directing an Internet user in need of smile-enhancing dentistry to find, evaluate and select a provider for dental services (namely dentures, crowns, veneers, dental implants, orthodontics, periodontics, and/or maxillofacial surgery), motivate her to pursue the predicted visual treatment results, inform her on issues related to achieving those results (i.e. costs, timeframes, procedures, etc.), then produce and provide physical devices that facilitate the treatment planning and procedural process. Specifically, the present invention is a platform that allows a user to evaluate and request services from network providers while streamlining the process for the dentist.

"Artificial intelligence" as used herein to broadly describe any computationally intelligent systems that combine knowledge, techniques, and methodologies. An AI engine may be any system configured to apply knowledge and that can adapt itself and learn to do better in changing environments. Thus, the AI engine may employ any one or combination of the following computational techniques: neural network, constraint program, fuzzy logic, classification, conventional artificial intelligence, symbolic manipulation, fuzzy set theory, evolutionary computation, cybernetics, data mining, approximate reasoning, derivative-free optimization, decision trees, and/or soft computing. Employing any computationally intelligent techniques, the AI engine may learn to adapt to unknown and/or changing environment for better performance.

As used herein, the term "computing device," refers to a device including a processing unit and having computing capabilities. Some examples of a computing device include a PC, laptop, tablet, or a smartphone having a display. In this example implementation, the computing device (CPU) may be coupled, connected, and/or in communication with a network via communication channels including, but not limited to Internet connections, satellite communications, wireless channels, cloud connections, etc.

As used herein, the term database refers to an organized collection of data with a software system designed to allow the definition, creation, querying, update, and administration of databases.

The term patient encompasses, but is not limited to, a recipient of health care services.

As used herein, the term platform refers to a computer software application hosted on a server, stored persistently on storage or memory available to the server, and executing on one or more computing devices of the server.

As used herein, the term server refers to a system (software and suitable computer hardware) that responds to requests across a computer network.

The present invention is represented by the Internet-accessible platform 8 allowing a patient to review the database of providers for dental services through use of a computing device 12. The network 10 represents the communication pathway between the patients' computing devices 12 and the online system stored on one or more servers 14. In one embodiment, the network 10 is the internet. The network 10 can also utilize dedicated or private communication links (e.g. WAN, MAN, or LAN) that are not necessarily part of the Internet. The networked patient devices 12 use standard communication technologies and/or protocols.

The patient computing devices 12 are used by the patients interacting with the online platform system 8. The device 12 executes an operating system, for example, a Microsoft Windows-compatible operating system (OS), Apple OS X or iOS, a Linux distribution, or Google's Android OS. In some embodiments, the device 12 may use a web browser, such as Microsoft Internet Explorer, Mozilla Firefox, Google Chrome, Apple Safari and/or Opera, as an interface to interact with the online platform. In other embodiment, the device 12 can execute a dedicated application for accessing the online platform 8.

The online platform 8 includes a server 14 that presents web pages or other web content, which form the basic interface to the patients. Patients use respective devices 12 to access one or more web pages, and provide data to the system through the online platform 8.

The online platform 8 may be for example a scheduling system, a provider referral system, a patient education system, a provider education system, and a third party payer verification/preauthorization system and the like. More generally, the online platform provides patients with access to a list of providers within a specified area for review by the patient. In some embodiments, the online platform 8 facilitates transactions between the patient and the provider. For example, a scheduling system allows patients to request appointments for dental consultation with the provider.

Those of skill in the art will appreciate that the online scheduling system will contain other modules appropriate for its functionality (e.g., social networking, banking, commerce, etc.), but that are not described herein, since they are not directly material to the invention. In addition, conventional elements, such as firewalls, authentication and encryption systems, network management tools, load balancers, and so forth are not shown as they are not material to the invention. The online scheduling system may be implemented using a single computer, or a network of computers, including cloud-based computer implementations. The computers are preferably server class computers including one or more high-performance computer processors and main memory, and running an operating system such as LINUX or variants thereof. The operations of the scheduling system as described herein can be controlled through either hardware or through computer programs installed in non-transitory computer storage and executed by the processors to perform the functions described herein. The database is implemented using non-transitory computer readable storage devices, and suitable database management systems for data access and retrieval. The database is implemented in a database management system, such as a relational database (e.g., MySQL). The scheduling system includes other hardware elements necessary for the operations described here, including network interfaces and protocols, input devices for data entry, and output devices for display, printing, or other presentations of data. As will become apparent below, the operations and functions of the scheduling system are sufficiently complex as to require implementation on a computer system, and cannot be performed as a practical matter in the human mind.

Figure 2:
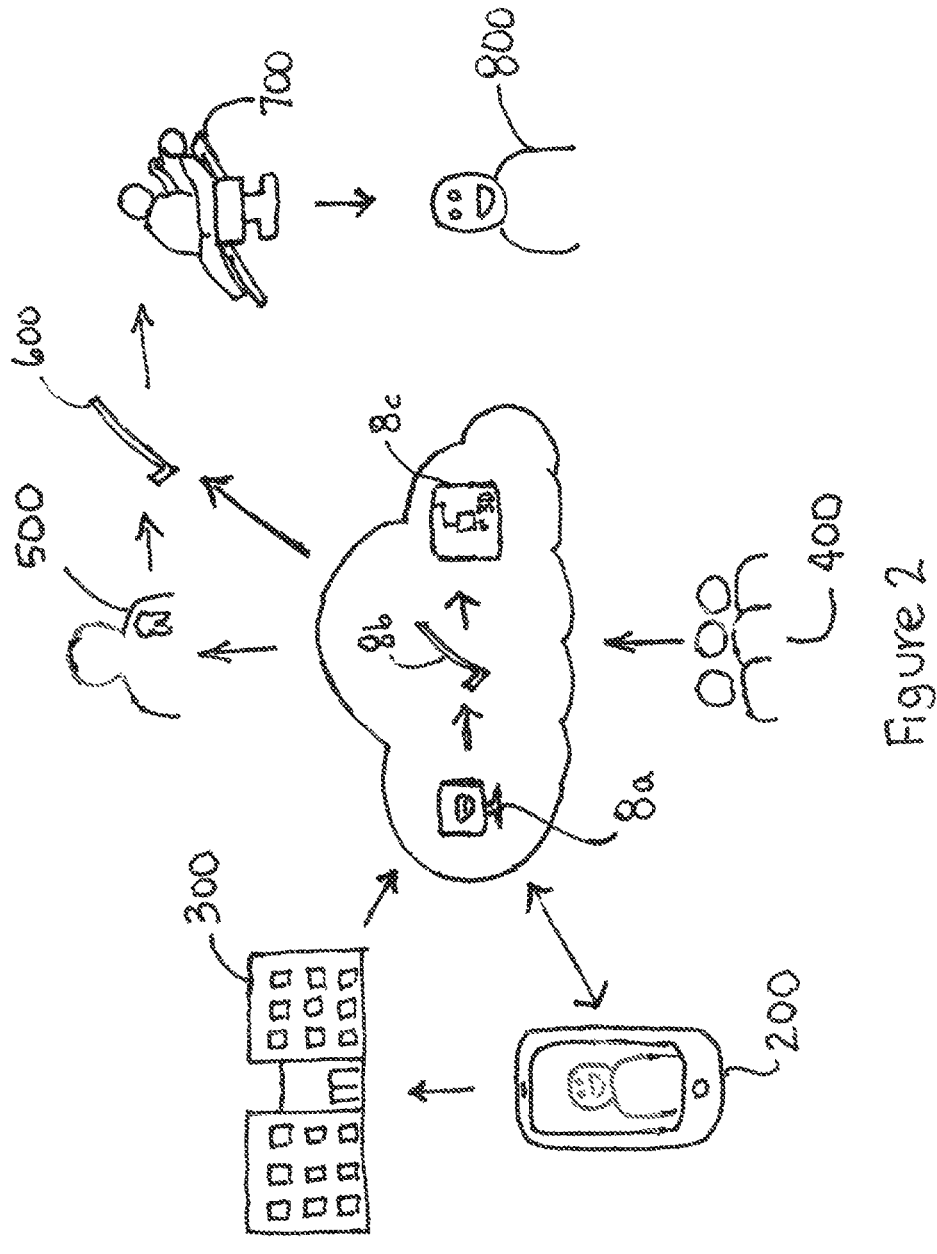
FIG. 2 is a schematic of the method of the present invention.

As detailed in FIG. 2, the scheduling system provides a patient scheduling interface and processing logic for providers to list available appointment times and availability and patients to select times for appointments. The user interface for the scheduling system requires a patient to provide either an image capture of the patient's face and teeth or an uploaded image to complete the reservation of the appointment in the system. The user interface may use prompts, such as a screen image in the interface that requests that the patient place the patient's face within the screen image for the image capture. The user interface may additionally direct the patient to a scanning facility local to the patient (i.e. a geographic location within an hour or less travel from the home address of the patient) or to a local provider location with a scanning mechanism. The uploaded digital images of the patient can be captured 200 through a camera module on the user device, through an upload module, or through a standalone facility the patient visits prior to visiting the provider. The user interface provides prompts to the scanning facility or to the patient accessing the user interface to provide 200 a facial image showing the face of the patient from multiple angles, including a front-facing image of the of the patient and a perspective view of the patient face to provide image data for the system to generate a digital image of the digital smile result for the patient post-treatment.

Additionally, the system may contain an artificial intelligence engine to aid in determining and/or identifying if the uploaded digital image of the patient does not meet the requirements of the system, namely if the uploaded digital image does not capture the whole face or does not show the teeth of the patient. The artificial intelligence engine may prompt the patient immediately after upload or at a later time to then request images to be uploaded to the system. The artificial intelligence engine could also propose an immediate digital smile preview through the use of facial tracking and augmented reality for initial patient visualization/motivation purposes.

Once the uploaded digital image is verified as a correct submission, the system utilizes an artificial intelligence engine to calculate patient information from the uploaded digital image, namely mouth dimensions for the patient.

The scheduling system allows the patient to include additional media, such as videos of the face, scans or images from home impression kits provided by mail to the patient, initial medical/dental history, dental/medical insurance information or information regarding the concerns of the patient to allow for the provider to assess the case prior to acceptance of the appointment. The information related to concerns of the patient may be generated from a series of prompts from the scheduling system. Appointment bookings with their photographic images 16 and additional media created by the patient scheduling interface are processed by the scheduling system and stored in the database on the server 14.

Subsequent to the submission of initial patient data (acquired and submitted by the patient 200 and/or a scanning center 300) through the platform, the digital smile design service is completed 8A to then be made available for review by the patient 200 for initial approval. Then area providers 400 are selected from a directory within the platform, and the prospective patient information and digital smile design preview is transmitted to those providers 400 per patient preference for case approval. The providers are notified of a potential new case for review via the platform, and once case acceptance is achieved 8B the first in-person appointment is scheduled between patient 200 and preferred, accepting provider 500.

With the digital smile design completed and treatment preview approved by patient and selected provider, the dental laboratory can prepare 8C initial dental assets for review by the provider and ship these assets to the provider for a try-in at the initial meeting.

The initial patient appointment now allows for the provider to directly review the digital images with the patient, complete the necessary clinical examination and direct diagnostics followed by a physical smile try-in using the asset(s) produced by the platform. Then a detailed treatment discussion can be had leading to a higher rate of case acceptance on the first encounter with the patient. As can be appreciated by one in the art, this would remove wasted time at the provider office for both the provider and the patient and lead to the patient accepting 600 the treatment proposal more readily and accomplish the actual treatment 700 more efficiently and predictably. The preemptive digital smile design and system for capturing and presenting a digitally altered treatment preview images increases clinical treatment success and patient satisfaction 800. In another embodiment of the present invention, the digitally altered image can be provided to the patient and the provider prior to the appointment, the provider can assess the estimated costs prior to the appointment with the patient.

The review module provides a patient interface and processing logic to receive reviews of the providers available to users, providing evaluations, feedback, and other commentary about a provider, and is one means for doing so. Completed reviews can be included within and appear alongside listings, so that future patients interested in seeking treatment from the provider can evaluate and select the provider with the reviews in mind. It is an object of the present invention to restrict reviews in the review module to confirmed patients of the provider. Reviews are stored alongside their associated provider listings in the database.

The search module provides a patient interface and processing logic for searching the database for providers responsive to a search query, and is one means for doing so. The patient interface of the search module is configured to receive a search query specifying various attributes of the provider, such as gender, location, price, and so forth. The search module matches the attributes of the search query to provider in the database, ranks the providers using the ranking module, and provides the ranked set of providers to a patient device, so that the user of the patient device can access the providers in a convenient manner. The patient interface of the search module is capable of displaying the ranked set of listings by rank order.

Figure 3:
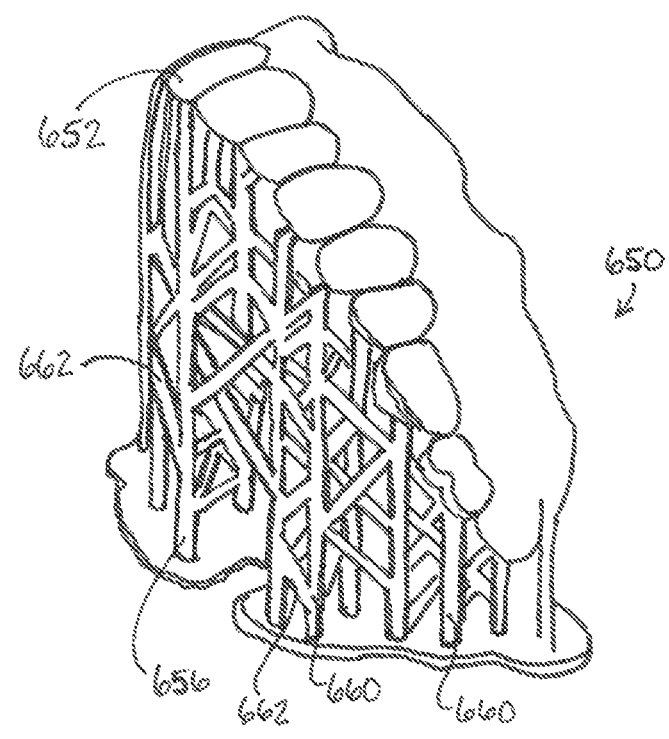
FIG. 3 is a perspective view of an embodiment of the present invention.
Figure 4:
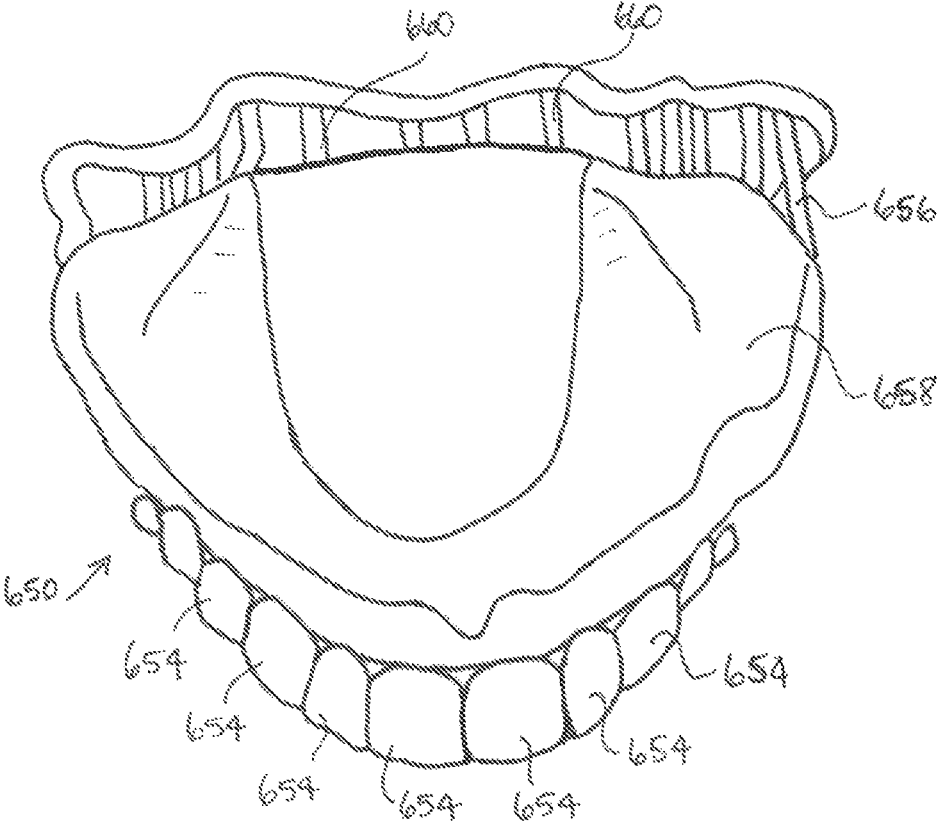
FIG. 4 is a top view of an embodiment of the present invention.
Figure 5:
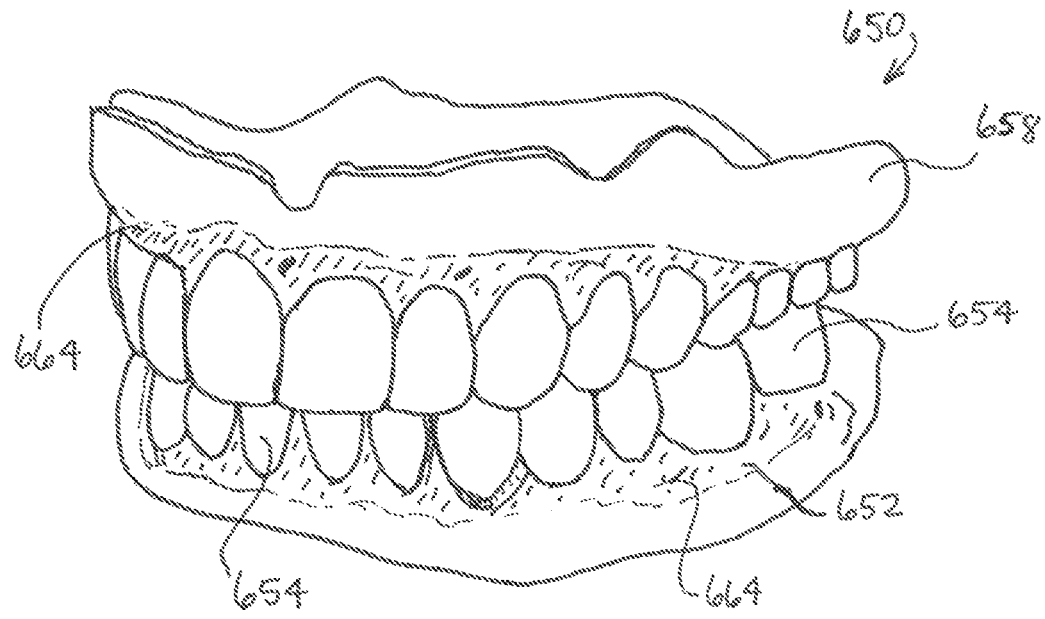
FIG. 5 is a front view of an embodiment of the present invention.

As shown in FIGS. 3-5, initial dental assets can be prepared by the provider or a dental laboratory for an initial try-in of the proposed correction. The initial dental assets can be prepared based upon the calculated patient data from the uploaded patient image. As it relates to complete dentures, the try-in model 650 may be fabricated by a method including prototyping equipment such as three-dimensionally printing the baseplate 658, and artificial teeth 654 in situ in proper spatial orientation. There is a need to create the artificial teeth as separate from the baseplate and separable from each other as some teeth may need to be moved or repositioned during the try-in process in order to meet patient and/or provider satisfaction.

The process of three-dimensionally printing the artificial teeth 654 separate from the baseplate and separable from each other requires orientation of the print support framework 656 such that the neck of each artificial tooth 654 is spatially separate from the baseplate only minimally connected to the adjacent teeth at the interproximal contact point to allow the artificial teeth to be printed in situ but remain easily modifiable during the try-in appointment. As shown, the try-in is oriented such that the print support framework 656 connects to the back/top surface of each tooth and separately to the baseplate surface allowing minimal (if any) physical connection between the artificial teeth and the baseplate. The framework 656 is three-dimensionally printed in thin layers 660 to provide a temporary structure during printing and positioned in the manner described to allow for secondary application of thermoplastic interstitial material (i.e. baseplate wax) 664 to secure the artificial teeth to the baseplate in the proper spatial orientation so that the print support framework can be removed without affecting the position of the artificial teeth relative to the baseplate but still allow for usual and customary modifications of the try-in as would be possible with a traditional denture try-in. The orientation of the framework 656, i.e. connected to the back/top surface of each tooth, allows easy application of baseplate wax to the gap between the baseplate and the teeth from the facial/buccal side as it is opposite the build support connections. The addition of the baseplate wax relinks the separate baseplate and teeth and maintains their orientation relative to each other and allows the removal of the framework 656 without changing the orientation of the teeth relative to the baseplate.

As discussed above, the teeth are printed to allow functional movement of the teeth as deemed necessary by the dentist easily and quickly by simply warming the baseplate wax and modifying the tooth positions when the wax is soft, then recooling. This is helpful to achieve any necessary cosmetic and/or functional tooth corrections, i.e. shifting the upper teeth to align with facial/intraoral landmarks and also to achieve optimal bite posturing.

The wax compound 664 can be any color, however the use of a pink color mimics natural gingiva and is more pleasing for the try-in. Once the wax is in place, the scaffolding can be cut from the back of the teeth without movement of the individual teeth.

In another embodiment of the try-in assets developed from the digital smile preview design, a physical model of the patient's teeth and oral tissues is created via rapid prototyping as a combined model of the dentition in its current state with the additional surfaces of the reconstructed teeth superimposed. From this physical model, a former (i.e.

a silicone mold or a thermoplastic vacuum-formed shell) can be created which is used to apply removable tooth colored material (i.e. dental composite resin, impression material, etc.) directly to the pre-treatment dentition for direct visualization of the proposed treatment results. Often these surfaces are modified in size, shape, and/or position to ensure adequate coverage of the problematic, pre-treatment tooth surfaces with enough prosthetic preview material for successful direct visualization at the in-office smile try-in appointment.

In another embodiment of the try-in assets, if the digital treatment design surfaces are modified to achieve adequate material bulk on the necessary visible and functional surfaces of the pre-treatment dentition, a physical model of those teeth can be produced directly via prototyping equipment (3D printing or computer numeric control milling) as a stand-alone anatomic overlay (i.e. snap-on-smile). Given the materials and methods with which this type of try-in appliance can be produced, these could be sent home with the patient for extended trial review purposes or even shipped directly to the patient before the first clinical appointment with a dentist.

Unless otherwise stated, all technical and scientific terms used herein have the same meaning as commonly understood by one of ordinary skill in the art to which this invention belongs. Although any methods and materials similar or equivalent to those described herein can also be used in the practice or testing of the present invention, a limited number of the exemplary methods and materials are described herein. It will be apparent to those skilled in the art that many more modifications are possible without departing from the inventive concepts herein.

All terms used herein should be interpreted in the broadest possible manner consistent with the context. In particular, the terms "comprises" and "comprising" should be interpreted as referring to elements, components, or steps in a non-exclusive manner, indicating that the referenced elements, components, or steps may be present, or utilized, or combined with other elements, components, or steps that are not expressly referenced. When a Markush group or other grouping is used herein, all individual members of the group and all combinations and subcombinations possible of the group are intended to be individually included. All references cited herein are hereby incorporated by reference to the extent that there is no inconsistency with the disclosure of this specification. When a range is stated herein, the range is intended to include all sub-ranges within the range, as well as all individual points within the range. When "about," "approximately," or like terms are used herein, they are intended to include amounts, measurements, or the like that do not depart significantly from the expressly stated amount, measurement, or the like, such that the stated purpose of the apparatus or process is not lost.

The present invention has been described with reference to certain preferred and alternative embodiments that are intended to be exemplary only and not limiting to the full scope of the present invention, as set forth in the appended claims.

The invention claimed is:

1. A method for producing a denture try-in for cosmetic and functional evaluation using a computerized system having a computing device with a processor and a three-dimensional printer, the denture try-in having a denture baseplate having a surface and artificial teeth, the method comprising the steps of:

a. providing a user interface of a platform for a computing device, said user interface having a prompt to receive patient information;

b. receiving through the user interface of the platform patient information comprising at least one digital image of the patient, said at least one digital image of the patient selected from the group consisting of an image showing the face of the patient, an image showing a front view of the face of the patient, or an image showing a perspective view of the patient;

c. calculating patient information from the at least one digital image of the patient;

d. generating a digital preview of a smile result based on the at least one digital image of the patient;

e. fabricating the denture baseplate via three-dimensional printing, the denture baseplate based upon the calculated patient information;

f. fabricating the artificial teeth separately from the denture baseplate via three-dimensional printing, the artificial teeth fabricated as a contiguous arch with each neck of each individual tooth spatially separate from the denture baseplate, each individual tooth of the artificial teeth fabricated in situ in proper spatial orientation relative to the denture baseplate and based upon the calculated patient information, each individual tooth having its neck region spatially separated from the denture baseplate and the contiguous arch being subdividable into groups or individual teeth to allow movement or positioning individually or in groups;

g. fabricating a removable print support framework via three-dimensional printing, the removable print structure framework connected to the back of the artificial teeth to maintain the contiguous arch of the artificial teeth in situ with each base of each individual tooth proximate the surface of the denture baseplate;

h. applying wax interface to the base of each individual tooth of the artificial teeth and the denture baseplate, the wax interface securing the artificial teeth to the denture baseplate while maintaining the contiguous arch of the artificial teeth;

i. removing the print support framework, whereby the artificial teeth remain secured by the wax; and j. selectively softening the wax interface to move or position one or more of the artificial teeth individually or in a group to achieve optimal bite-posturing or to align with facial or intraoral landmarks.

2. A method of producing for a patient a denture try-in with a denture baseplate having a surface and artificial teeth using a computerized system having a computing device with a processor and a three-dimensional printer, the method comprising:

a. receiving through a patient information platform at least one digital image of the patient, said at least one digital image of the patient selected from the group consisting of an image showing the face of the patient, an image showing a front view of the face of the patient, or an image showing a perspective view of the patient;

b. fabricating the denture baseplate via three-dimensional printing based on the at least one digital image of the patient;

c. fabricating the artificial teeth via three-dimensional printing separately from the denture baseplate with each neck of each individual tooth spatially separate from the denture baseplate, each individual tooth of the artificial teeth fabricated in situ in proper spatial orientation based upon the calculated patient information, whereby each individual tooth of the artificial teeth may be moved and positioned individually or in groups;

d. fabricating a removable print support framework via three-dimensional printing connected to the back of the artificial teeth to maintain the artificial teeth in situ with each base of each individual tooth proximate the surface of the denture baseplate;

e. applying wax to the base of each individual tooth of the artificial teeth and the denture baseplate, the wax securing the artificial teeth to the denture baseplate;

f. removing the print support framework; and g. selectively softening the wax to move or position one or more the artificial teeth individually or in a group to achieve optimal bite-posturing or to align with facial or intraoral landmarks.

3. A method of producing for a patient a denture try-in with a denture baseplate having a surface and artificial teeth, the method comprising:

a. fabricating the denture baseplate;

b. fabricating the artificial teeth separately from the denture baseplate with each neck of each individual tooth spatially separate from the denture baseplate, each individual tooth of the artificial teeth fabricated in situ in proper spatial orientation, whereby each individual tooth of the artificial teeth may be moved and positioned individually or in groups;

c. fabricating a print support framework connected to the back of the artificial teeth to maintain the artificial teeth in situ with each base of each individual tooth proximate the surface of the denture baseplate;

d. applying wax to the base of each individual tooth of the artificial teeth and the denture baseplate, whereby the artificial teeth are connected to the denture baseplate prior to any removal of the print support framework;

e. removing the print support framework; and f. selectively softening the wax to move or position one or more the artificial teeth individually or in a group to achieve optimal bite-posturing or to align with facial or intraoral landmarks.

* * * * *